US011998233B2

(12) United States Patent
Pyles

(10) Patent No.: US 11,998,233 B2
(45) Date of Patent: Jun. 4, 2024

(54) DIRECTIONAL DEVICE FOR EPIDURAL NEEDLE

(71) Applicant: Spiro Medical, Inc., Belleair Bluffs, FL (US)

(72) Inventor: Stephen T. Pyles, Ocala, FL (US)

(73) Assignee: Spiro Medical, Inc., Belleair Bluffs, FL (US)

( * ) Notice: Subject to any disclaimer, the term of this patent is extended or adjusted under 35 U.S.C. 154(b) by 698 days.

(21) Appl. No.: 17/113,232

(22) Filed: Dec. 7, 2020

(65) Prior Publication Data
US 2022/0175415 A1  Jun. 9, 2022

(51) Int. Cl.
*A61B 17/34* (2006.01)
*A61B 90/00* (2016.01)

(52) U.S. Cl.
CPC ...... *A61B 17/3403* (2013.01); *A61B 17/3401* (2013.01); *A61B 90/37* (2016.02); *A61B 90/39* (2016.02); *A61B 2017/3407* (2013.01); *A61B 2017/3411* (2013.01); *A61B 2090/376* (2016.02); *A61B 2090/3937* (2016.02)

(58) Field of Classification Search
CPC . A61B 17/3403; A61B 17/3401; A61B 90/37; A61B 90/39; A61B 2017/3407; A61B 2017/3411; A61B 2090/376; A61B 2090/3937; A61B 2090/395; A61B 2090/3966; A61N 1/0551; A61N 1/36062; A61N 1/372; A61N 1/37241; A61N 1/36071
See application file for complete search history.

(56) References Cited

U.S. PATENT DOCUMENTS

| 5,669,882 A | 9/1997 | Pyles |
| 6,002,964 A * | 12/1999 | Feler ............... A61N 1/0551 |
| | | 607/46 |
| 6,689,142 B1 * | 2/2004 | Tremaglio, Jr. ... A61B 17/3496 |
| | | 604/114 |
| 8,029,495 B2 | 10/2011 | Pyles |
| 8,073,543 B2 | 12/2011 | Pyles |
| 8,463,385 B2 | 6/2013 | Pyles |
| 8,486,023 B2 | 7/2013 | Pyles |
| 9,078,690 B2 | 7/2015 | Pyles et al. |

(Continued)

FOREIGN PATENT DOCUMENTS

WO   2015179304 A1   11/2015

OTHER PUBLICATIONS

International Search Report and Written Opinion for Application No. PCT/US2021/062234 dated Apr. 7, 2022.

*Primary Examiner* — Amanda K Hulbert
*Assistant Examiner* — Natasha Patel
(74) *Attorney, Agent, or Firm* — Merchant & Gould P.C.

(57) ABSTRACT

A device is described for marking a path on a skin surface for inserting an epidural needle into an epidural space. The device includes a first arm having one or more holes spaced apart along the length of the first arm. A pin is attached at the proximal end of the first arm. A second arm has a proximal end attached to the pin allowing the first and second arms to rotate about the pin to adjust an angle separating the first and second arms. The second arm has one or more holes spaced apart along the length of the second arm. The holes on the first and second arms provide locations for marking the path on the skin surface to insert the epidural needle.

16 Claims, 10 Drawing Sheets

(56) References Cited

U.S. PATENT DOCUMENTS

| | | |
|---|---|---|
| 2005/0283046 A1 | 12/2005 | Pyles |
| 2005/0283216 A1 | 12/2005 | Pyles |
| 2006/0052765 A1 | 3/2006 | Pyles et al. |
| 2006/0206182 A1 | 9/2006 | Pyles |
| 2008/0039866 A1 | 2/2008 | Stetz et al. |
| 2010/0114283 A1 | 5/2010 | King |
| 2010/0228251 A1 | 9/2010 | Hörlle |
| 2012/0029467 A1 | 2/2012 | Pyles et al. |
| 2014/0005604 A1 | 1/2014 | Murphy et al. |
| 2015/0164519 A1 | 6/2015 | Cheng |
| 2015/0272610 A1 | 10/2015 | Pyles et al. |
| 2016/0001066 A1 | 1/2016 | Pyles et al. |
| 2017/0095658 A1 | 4/2017 | Pyles et al. |
| 2019/0231470 A1* | 8/2019 | Fink ........................ A61B 90/11 |

* cited by examiner

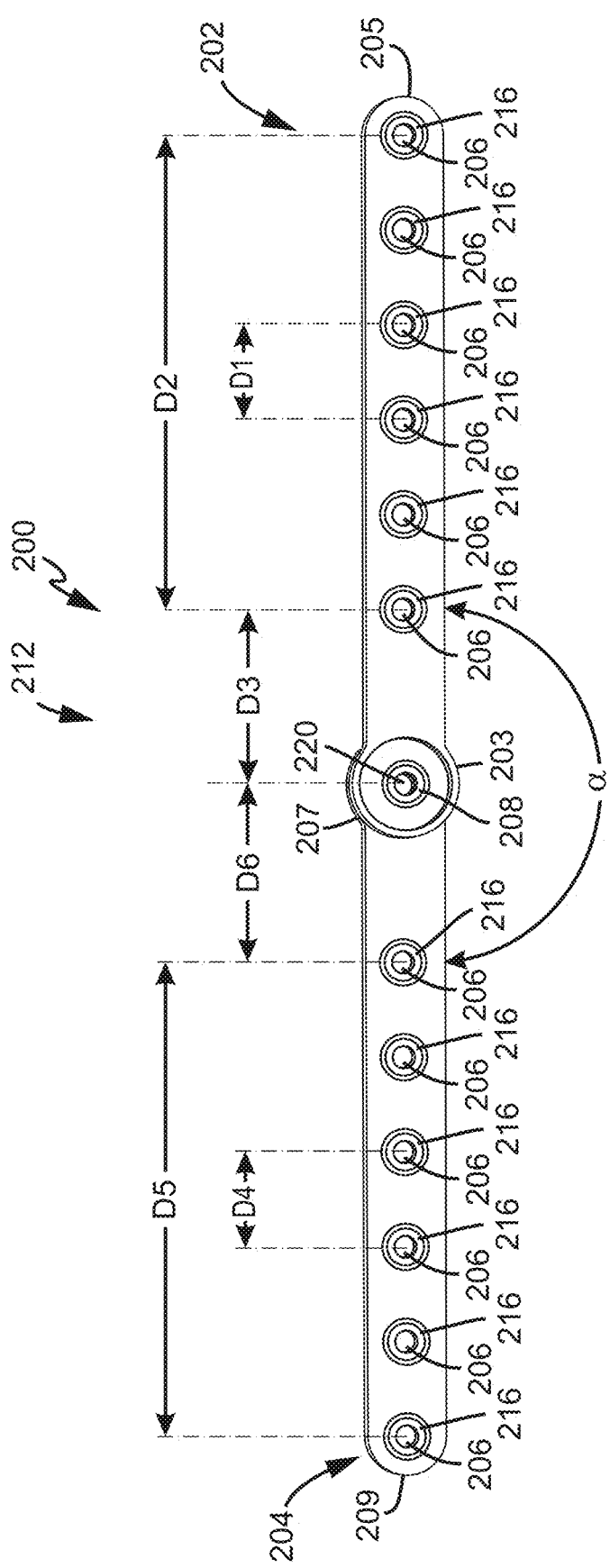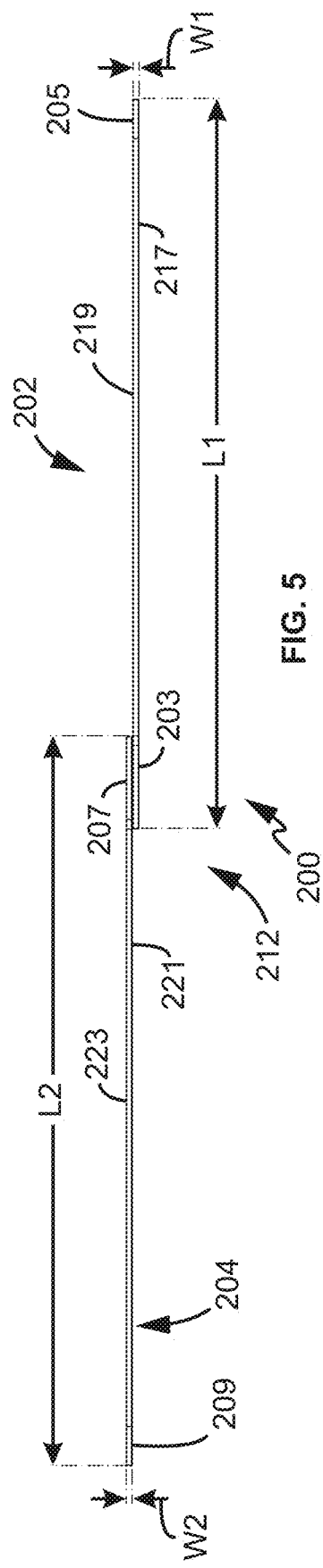
FIG. 4
FIG. 5

DIRECTIONAL DEVICE FOR EPIDURAL NEEDLE

BACKGROUND

Spinal cord stimulation (SCS), also known as dorsal column stimulation (DCS), is typically performed by physicians to provide pain relief for patients suffering from chronic intractable pain. SCS uses electrical impulses to relieve chronic pain of the back, arms, and legs. The electrical impulses prevent pain signals from being received by the brain. SCS is typically performed for patients who suffer from neuropathic pain (i.e., pain marked by burning, tingling or numbness) and for whom traditional pain relief treatments have failed.

Unlike other surgical procedures, a trial SCS procedure is performed before offering a patient a permanent SCS surgical implant. The trial SCS procedure is typically preformed in the physician's office or in an outpatient surgical facility, and includes implanting temporary SCS leads into the posterior epidural space of the patient's spine using an epidural needle.

Physicians new to the SCS procedure often have difficulty inserting the epidural needle at a correct angle which has clinically been shown to improve the probability that the SCS lead will pass through the epidural needle and into the posterior epidural space as it is advanced. SCS leads must be placed in the posterior epidural space to be effective. If the SCS leads are placed anteriorly, the spinal cord cannot be properly stimulated, and the benefit provided by the trial SCS procedure is lost.

SUMMARY

In general terms, the present disclosure relates to spinal cord stimulation. In one possible configuration, a device provides visual guidance to assist a physician in inserting an epidural needle to implant a SCS lead into the epidural space of the spine. Various aspects are described in this disclosure, which include, but are not limited to, the following aspects.

One aspect relates to a device for marking a path on a skin surface for inserting an epidural needle into an epidural space. The device comprising a first arm having a length extending between a proximal end and a distal end, and one or more holes spaced apart along the length of the first arm; a pin attached at the proximal end of the first arm; and a second arm having a proximal end attached to the pin allowing the first and second arms to rotate about the pin to adjust an angle separating the first and second arms, and further having a length extending from the proximal end to a distal end, and one or more holes spaced apart along the length of the second arm; wherein the one or more holes on the first and second arms provide locations for marking the path on the skin surface to insert the epidural needle.

Another aspect relates to a kit for marking a path on a skin surface for inserting an epidural needle into an epidural space. The kit comprising a writing instrument; and a device comprising: a first arm having a length extending between a proximal end and a distal end, and one or more holes spaced apart along the length of the first arm; a pin attached at the proximal end of the first arm; and a second arm having a proximal end attached to the pin allowing the first and second arms to rotate about the pin to adjust an angle separating the first and second arms, and further having a length extending from the proximal end to a distal end, and one or more holes spaced apart along the length of the second arm; wherein the one or more holes on the first and second arms provide locations for using the writing instrument to mark the path on the skin surface to insert the epidural needle.

Another aspect relates to a method of using a device to prepare a patient for implantation of a lead for spinal cord stimulation, the method comprising positioning the device over a target location for implanting the lead; adjusting an angle separating first and second arms of the device to define a path for inserting an epidural needle to reach an epidural space of the target location; and inserting a writing instrument into one or more holes on the first and second arms of the device to mark the path on a skin surface of the patient.

A variety of additional aspects will be set forth in the description that follows. The aspects can relate to individual features and to combination of features. It is to be understood that both the foregoing general description and the following detailed description are exemplary and explanatory only and are not restrictive of the broad inventive concepts upon which the embodiments disclosed herein are based.

DESCRIPTION OF THE FIGURES

The following drawing figures, which form a part of this application, are illustrative of the described technology and are not meant to limit the scope of the disclosure in any manner.

FIG. 4 is a top view of the device in an opened position.

FIG. 5 is a side view of the device in the opened position.

DETAILED DESCRIPTION

Figure 1:
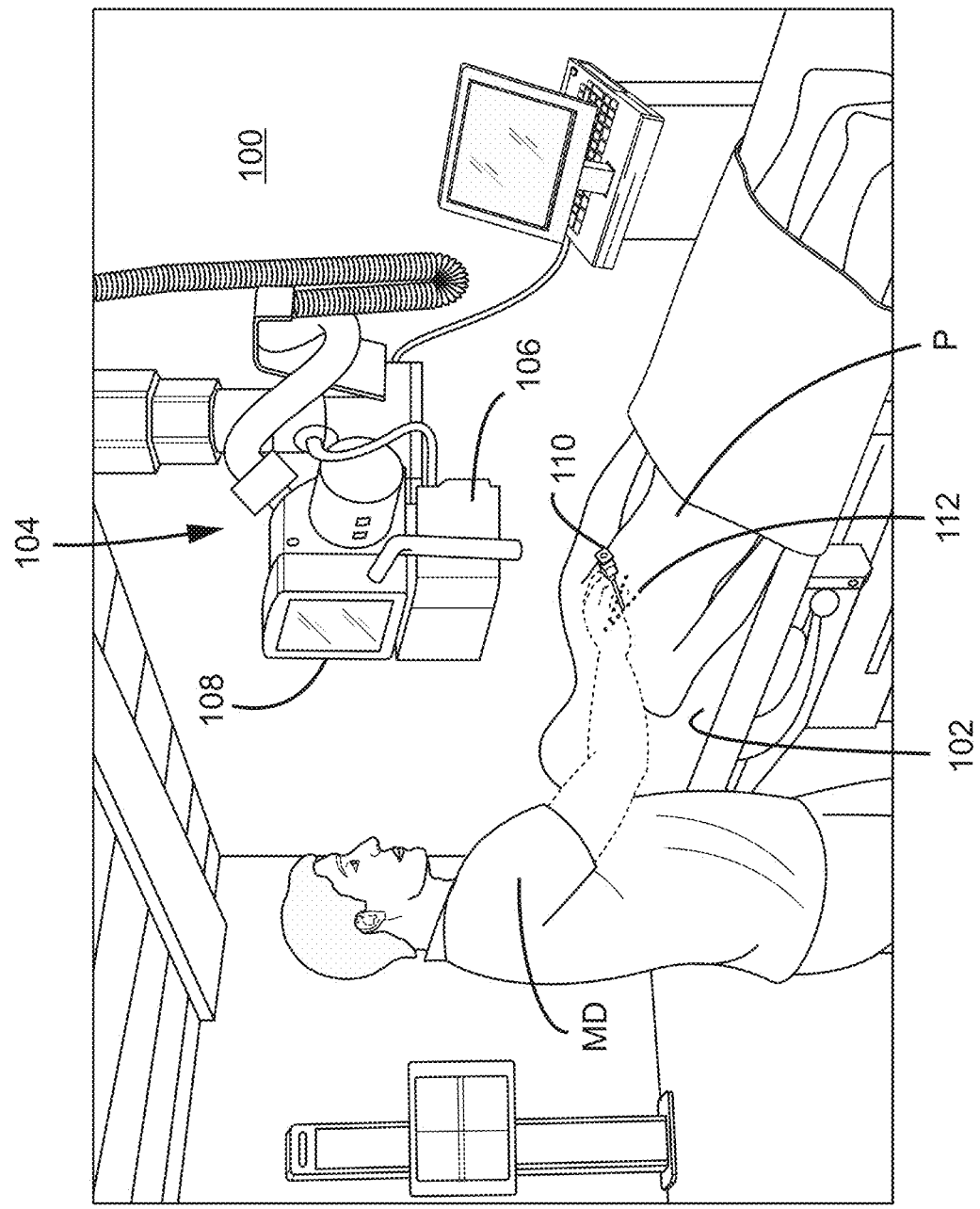
FIG. 1 illustrates an example system for performing a procedure using an epidural needle to implant one or more leads for spinal cord stimulation (SCS).

FIG. 1 illustrates an example system 100 for performing a procedure using an epidural needle 110 to implant one or more leads for spinal cord stimulation (SCS). In some examples, the epidural needle 110 is used to implant temporary percutaneous leads for a trial SCS procedure. In alternative examples, the epidural needle 110 is used to implant permanent percutaneous leads. The system 100 includes a table 102 on which the patient P rests face down. The patient P's back is exposed for a physician MD to insert the epidural needle 110.

The epidural needle 110 can be a 13 G or 14 G needle that is inserted into the skin, and through the paravertebral muscles until it reaches the lamina next to the spinous process located just below a selected target location in the epidural space the patient P's spine. The epidural needle 110 is then advanced through the ligamentum flavum and into the epidural space.

The system 100 includes a fluoroscopy system 104 that has at least an imaging device 106 that captures fluoroscopy images (i.e., X-ray images) of the patient P's spine, and a display device 108 that displays the fluoroscopy images for viewing by the physician MD. The physician MD can view the fluoroscopy images while inserting the epidural needle 110 into the patient P's epidural space, and while implanting the leads into the patient P's epidural space.

As an illustrative example, the physician MD inserts the epidural needle 110 into the epidural space of the patient P's spine, and thereafter threads one or more insulated wire leads through the epidural needle 110 to implant the distal ends of the leads into the epidural space. The leads are implanted into the epidural space to ensure that the leads are effective in providing the desired pain relief from SCS. The angle at which the epidural needle 110 is inserted into the patient P's spine can determine whether the leads successfully reach the posterior epidural space.

As shown in FIG. 1, a pattern of markings 112 are drawn on the patient P's back. The pattern of markings 112 are used by the physician MD as a path for inserting the epidural needle 110 into the patient P's spine at the correct angle. As will be described in more detail, the pattern of markings 112 is drawn by using a device 200 shown in FIGS. 2-7.

Figure 2:
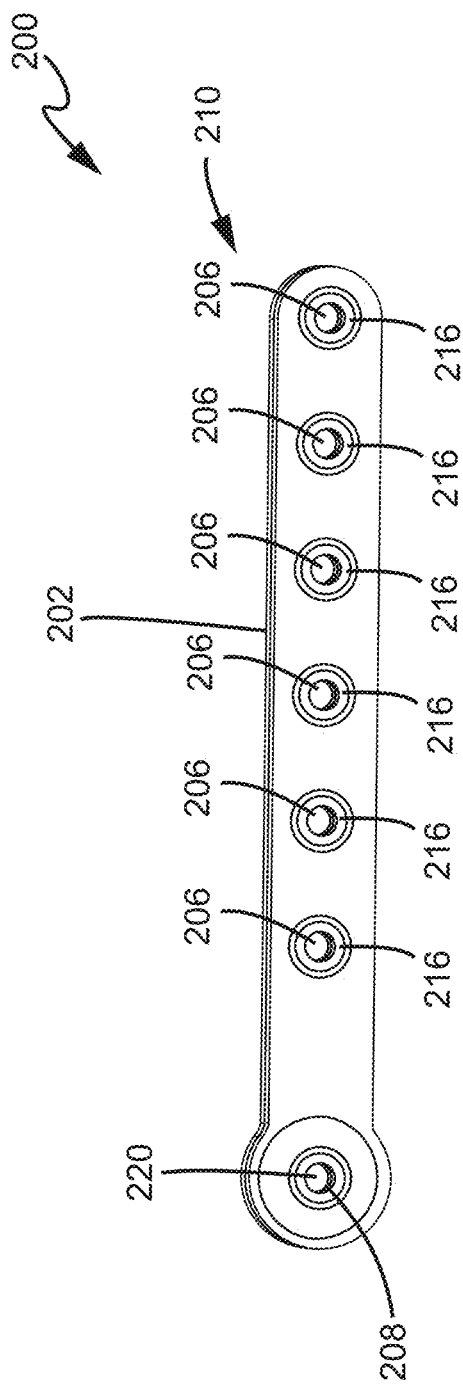
FIG. 2 is a top view of a device for marking a path on a skin surface for inserting the epidural needle into an epidural space for implanting the one or more leads for SCS, the device being shown in a closed position.
Figure 3:
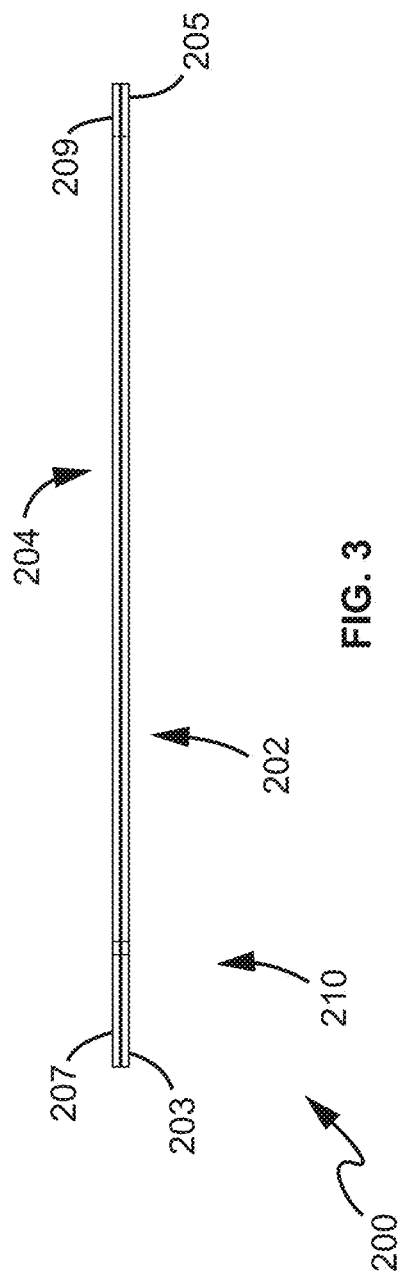
FIG. 3 is a side view of the device in the closed position.
Figure 6:
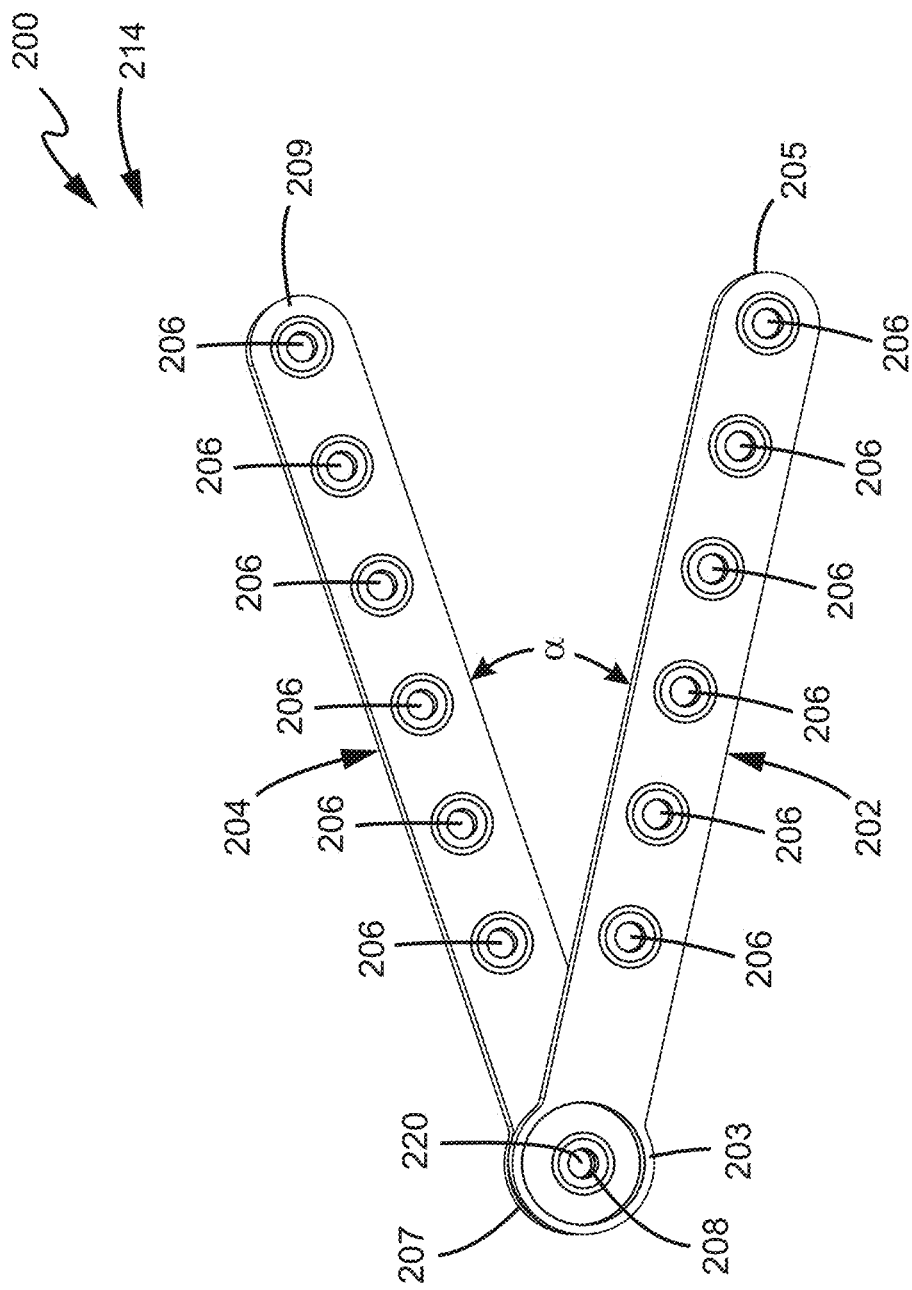
FIG. 6 is a top view of the device in an intermediate position that is adjustable between the opened and closed positions.

FIGS. 2 and 3 are views of the device 200 in a closed position 210, FIGS. 4 and 5 are views of the device 200 in an opened position 212, and FIG. 6 is a view of the device 200 in an intermediate position 214 that is adjustable between the closed and opened positions 210, 212. As shown in FIGS. 2-6, the device 200 includes a first arm 202, and a second arm 204 that is rotatably attached to the first arm 202 by a pin 208.

As shown in FIGS. 4 and 5, the first arm 202 has a length L1 extending between a proximal end 203 and a distal end 205. In the figures, the proximal and distal ends 203, 205 of the first arm are rounded and have a substantially semi-circular shape. It is contemplated that in alternative examples, the proximal and distal ends 203, 205 can have different shapes. In certain examples, the length L1 of the first arm 202 is about 10 cm to about 14 cm long (e.g., from 10 cm to 14 cm long). In certain examples, the length L1 of the first arm 202 is about 12 cm.

As shown in FIG. 5, the first arm 202 has a width W1 that separates a top surface 217 from a bottom surface 219. The first arm 202 is made from a material that is not visible in the fluoroscopy imaging generated on the display device 108 such that the top and bottom surfaces 217, 219 do not interfere with viewing the anatomical structures of the spine, such as is shown in the fluoroscopy image 900 of FIG. 9 which is described in more detail below.

The first arm 202 includes one or more holes 206 that extend through the width W1 from the top surface 217 to the bottom surface 219, and that are spaced apart along the length L1. In certain examples, the holes 206 on the first arm 202 are equally spaced apart.

The holes 206 on the first arm 202 are spaced apart from one another by a distance D1. In certain examples, the distance D1 is about 1 cm to about 2 cm (e.g., from 1 cm to 2 cm). A hole 206 located at the distal end 205 of the first arm 202 is separated from a hole 206 located at the proximal end 203 of the first arm by a distance D2. In certain examples, the distance D2 is about 6 cm to about 10 cm (e.g., from 6 cm to 10 cm). The hole 206 at the proximal end 203 of the first arm 202 is separated from a pin 208 by a distance D3. In certain examples, the distance D3 is about 2 cm to about 4 cm (e.g., from 2 cm to 4 cm). The foregoing distances D1-D3 are provided as illustrative examples, and these distances may vary as needed.

Figure 7:
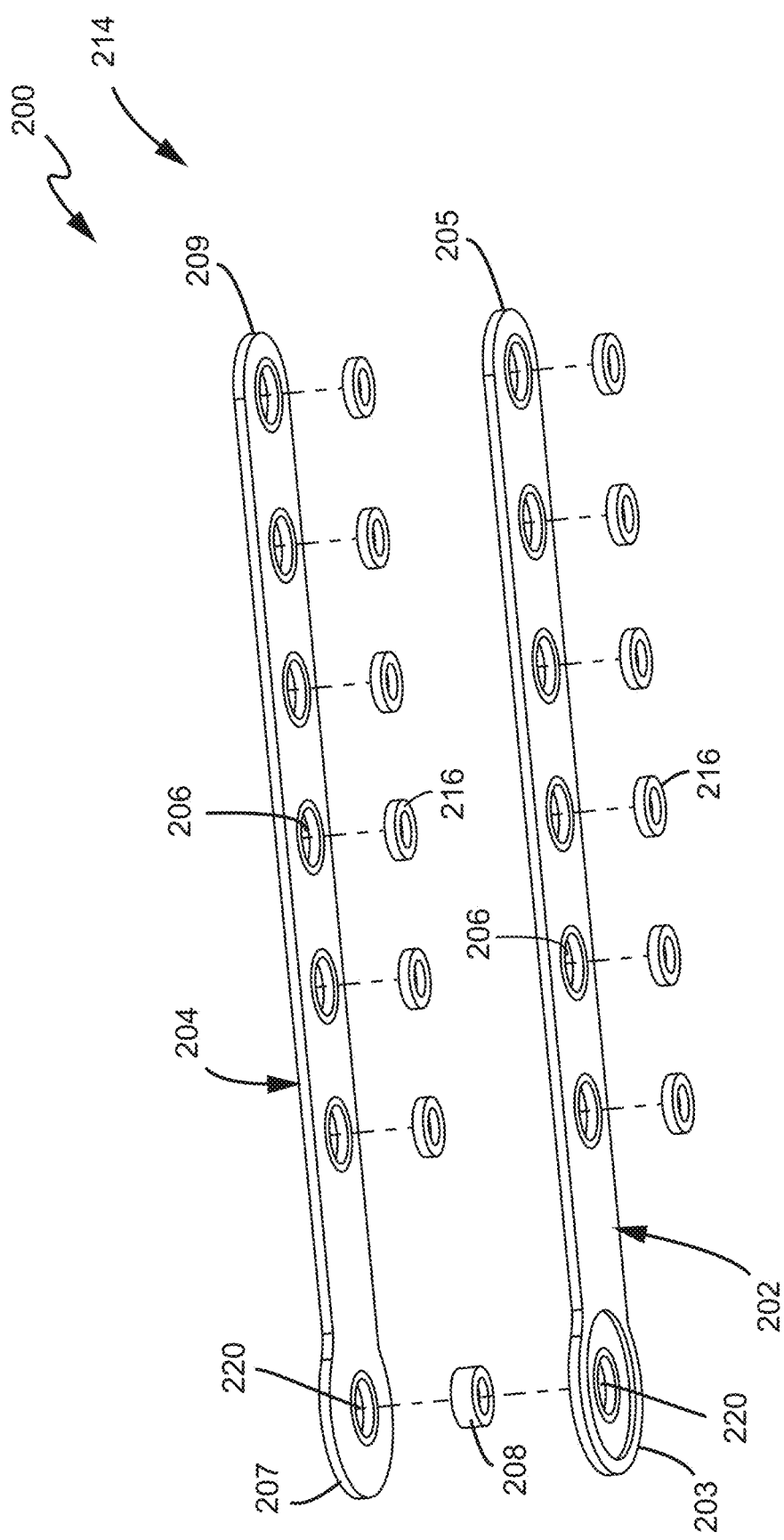
FIG. 7 is an exploded isometric view of the device.

FIG. 7 is an exploded isometric view of the device 200. Referring now to FIGS. 2-7, each hole 206 of the first arm 202 is surrounded by a material that is visible in fluoroscopy imaging generated on the display device 108 (see FIG. 9). For example, each hole 206 can include a grommet 216. In certain examples, each grommet 216 can include a flange at each end to provide surfaces for attachment to the top and bottom surfaces 217, 219 of the first arm 202. In certain examples, each grommet 216 is made from stainless steel or similar materials.

While the example of FIGS. 2-7 shows the first arm 202 having six holes, the first arm 202 can have more than six holes or fewer than six holes. Also, while the figures show the one or more holes 206 on the first arm 202 as having a circular shape, alternative shapes, sizes, and orientations for the one or more holes 206 are also contemplated such that the holes shown in the figures are provided by way of illustrative example and are not intended to be limiting.

For example, in some alternative embodiments, the first arm 202 includes a single hole instead of a plurality of holes. In such alternative embodiments, the single hole can be a longitudinal slot that extends along the length L1 of the first arm 202. Also, in such alternative embodiments, the longitudinal slot can have a liner made from a durable material such as stainless steel that is visible in fluoroscopy imaging provided on the display device 108.

The pin 208 is attached to the proximal end 203 of the first arm 202, and is attached to a proximal end 207 of a second arm 204. In certain examples, the pin 208 is a cylinder that extends across the width W1 of the first arm 202 and a width W2 of the second arm 204.

The pin 208 is hollow cylindrical tube that defines a hole 220. The pin 208 is made from a durable material that is visible in fluoroscopy imaging generated on the display device 108. In certain examples, the pin 208 is made from stainless steel or other similar materials.

A writing instrument can be inserted into the hole 220 to mark a target location on a skin surface of the patient P's back. As will be described in more detail, the target location is selected for implanting one or more SCS leads into an epidural space of the patient P's spine.

In certain examples, the pin 208 can include flanges at opposite ends that provide additional surfaces for attachment to the first and second arms 202, 204. For example, a flange at one end of the pin 208 can attach to the top surface 217 of the first arm 202, and a flange at an opposite end of the pin 208 can attach to a bottom surface 223 of the second arm 204.

The second arm 204 has a length L2 that extends from the proximal end 207 to a distal end 209. The proximal and distal ends 207, 209 of the second arm 204 are rounded and have a substantially semi-circular shape. In alternative examples, the proximal and distal ends 207, 209 can have different shapes and sizes. In certain examples, the length L2 of the second arm 204 is about 10 cm to about 14 cm long (e.g., 10 cm to 14 cm long). In certain examples, the lengths L1, L2 of the first and second arms 202, 204 are about the same or equal.

The width W2 of the second arm 204 separates a top surface 221 from the bottom surface 223. The second arm 204 is made from the same material as the first arm 202 such that the second arm 204 is not visible in the fluoroscopy imaging on the display device 108.

The second arm 204 includes one or more holes 206 that extend through the width W2 from the top surface 221 to the bottom surface 223, and that are spaced apart along the length L2 of the second arm 204. In certain examples, the one or more holes 206 on the second arm 204 are equally spaced apart along the length L2 of the second arm 204.

The holes 206 on the second arm 204 are spaced apart from one another by a distance D4. In certain examples, the distance D4 is about 1 cm to about 2 cm (e.g., from 1 cm to 2 cm). A hole 206 located at the distal end 209 of the second arm 204 is separated from a hole 206 located at the proximal end 207 of the second arm 204 by a distance D5. In certain examples, the distance D5 is about 6 cm to about 10 cm (e.g., from 6 cm to 10 cm). The hole 206 at the proximal end 207 of the second arm 204 is separated from the pin 208 by a distance D6. In certain examples, the distance D6 is about 2 cm to about 4 cm (e.g., from 2 cm to 4 cm). The foregoing distances D4-D6 are provided as illustrative examples and may vary.

In certain examples, the distances D4, D5, and D6 of the second arm 204 are equal to the distances D1, D2, and D3 of the first arm 202, respectively. Accordingly, in such examples the holes 206 on the first and second arms 202, 204 align with one another when the first and second arms 202, 204 are in the closed position 210, as shown in FIG. 2.

Figure 9:
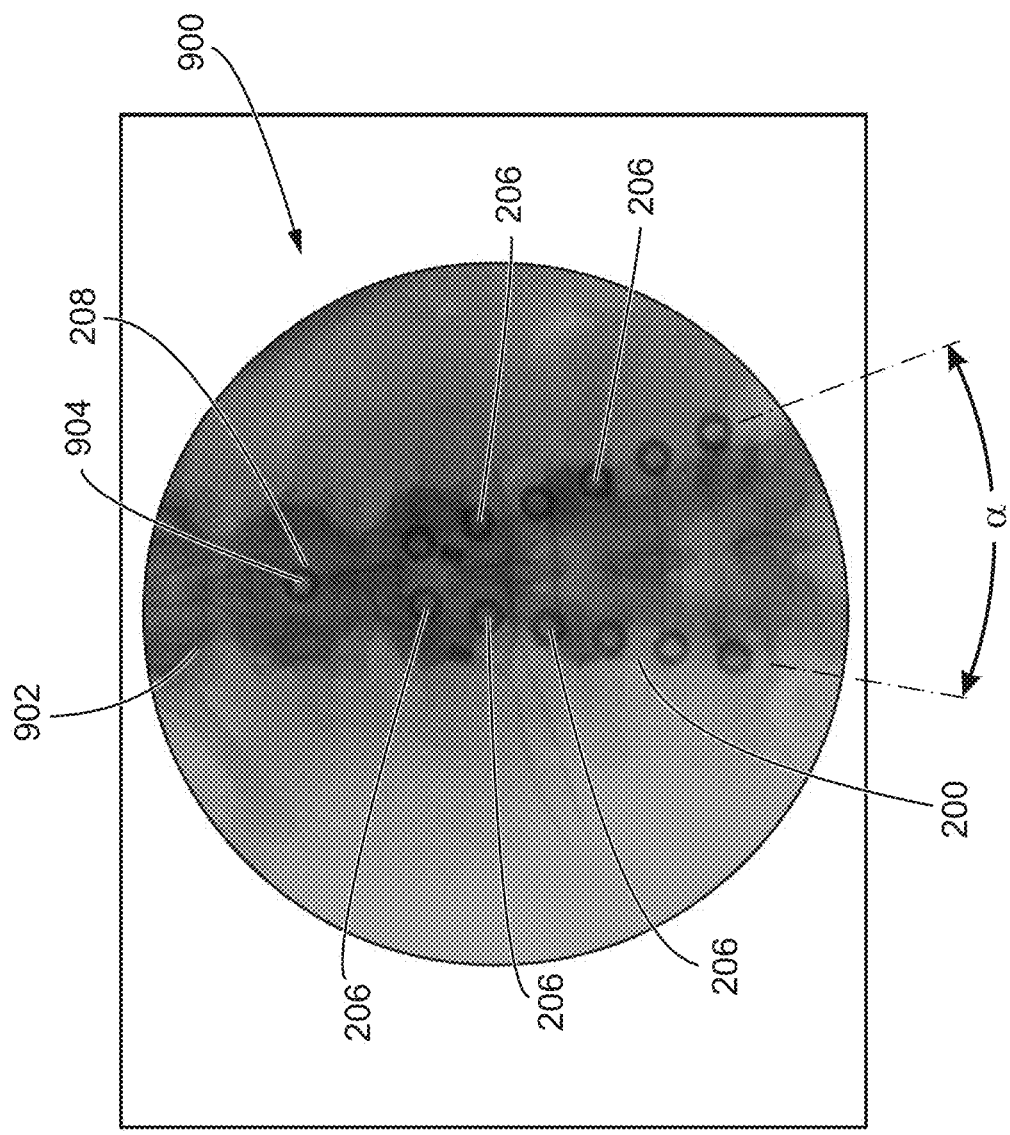
FIG. 9 is a fluoroscopy image of the spine with the device placed on top.

Each hole 206 of the second arm 204 is surrounded by a material that is visible in fluoroscopy imaging generated on the display device 108 (see FIG. 9). For example, each hole 206 can include a grommet 216. In certain examples, the each grommet 216 includes a flange at each end to provide surfaces for attachment to the top and bottom surfaces 221, 223 of the second arm 204. In certain examples, each grommet 216 on the second arm 204 is made from the same material as the grommets on the first arm 202 such as stainless steel or similar materials.

While the examples of FIGS. 2-7 show the second arm 204 as having six holes, it is possible for the second arm 204 to have more than six holes or fewer than six holes. Also, while the figures show the one or more holes 206 on the second arm 204 as having a circular shape, alternative shapes, sizes, and orientations for the one or more holes 206 on the second arm 204 are also contemplated such that the holes 206 on the second arm 204 that are shown in the figures are provided by way of illustrative example and are not intended to be limiting.

For example, in some alternative embodiments, the second arm 204 includes a single hole instead of a plurality of holes. In such alternative embodiments, the single hole can be a longitudinal slot that extends along the length L2 of the second arm 204. Furthermore, in such alternative embodiments, the longitudinal slot can have a liner made from a durable material that is visible in fluoroscopy imaging generated on the display device 108 such as stainless steel.

The proximal end 207 of the second arm 204 is attached to the pin 208 allowing the first and second arms 202, 204 to rotate about the pin 208 between the closed position 210 (see FIGS. 2 and 3) and the opened position 212 (see FIGS. 4 and 5). The first and second arms 202, 204 define an angle α that separates the first and second arms 202, 204 from one another. The angle α is 0 degrees when the first and second arms 202, 204 are in the closed position 210 (see FIG. 2). The angle α is 180 degrees when the first and second arms 202, 204 are in the opened position 212 (see FIG. 4). The angle α is between 0 degrees and 180 degrees when the first and second arms 202, 204 are in the intermediate position 214, as is shown in FIG. 6.

As will be described in more detail, the first and second arms 202, 204 are rotatable about the pin 208 to adjust the angle α of the intermediate position 214 between the closed and opened positions 210, 212 to draw the markings 112 (see FIG. 1) for inserting the epidural needle 110. For example, the holes 206 on the first and second arms 202, 204 provide locations for inserting a writing instrument to draw the marking 112 on the patient P's back.

Figure 8:
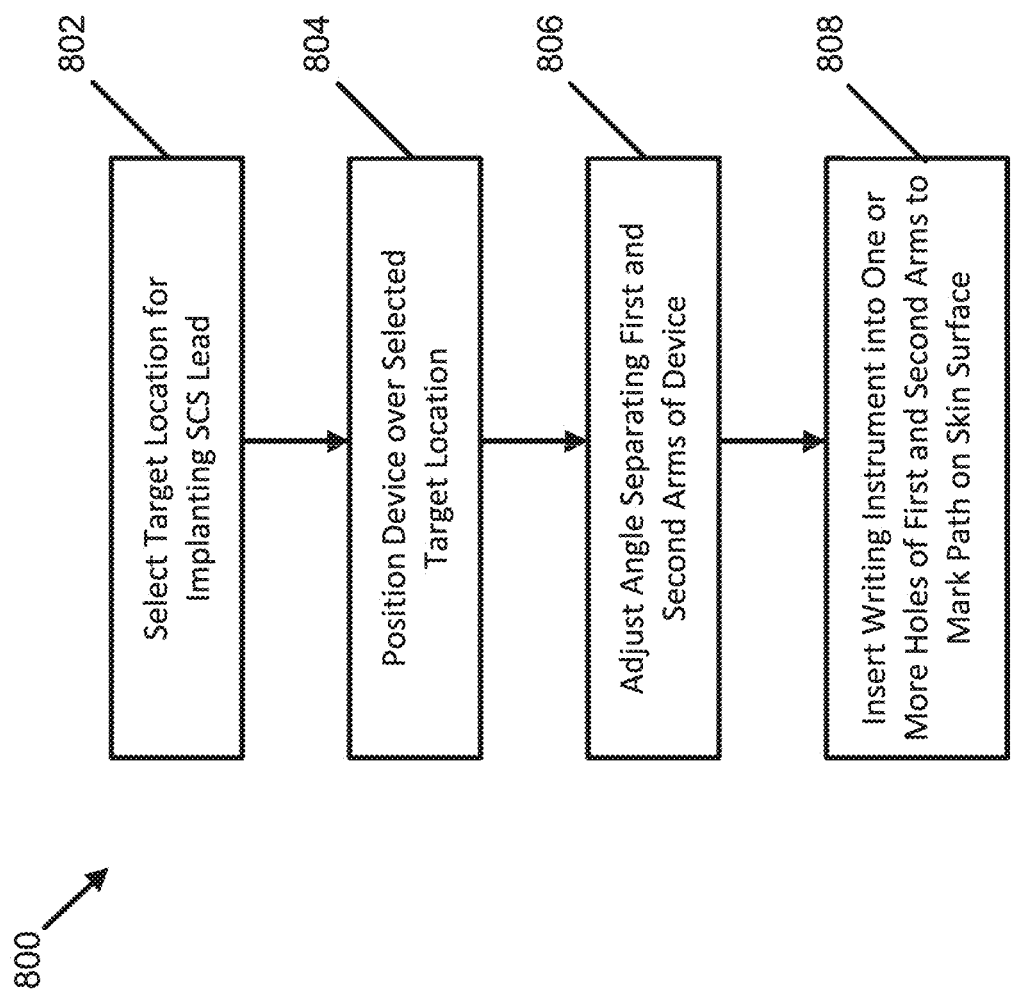
FIG. 8 illustrates a method of using the device to prepare a patient for a trial spinal cord stimulation procedure.

FIG. 8 illustrates a method 800 of preparing the patient P for implanting a temporary lead for spinal cord stimulation. At least one goal of the method 800 is to mark a path on the patient P's back for inserting the epidural needle 110 into the epidural space of the patient P's spine where a target location is identified for implanting one or more SCS leads.

The method 800 includes a step 802 of selecting a target location for implanting the one or more SCS leads. As described above, the target location is in the epidural space of the spine. The target location on the patient P's spine can be identified by viewing fluoroscopy imaging on the display device 108 of the fluoroscopy system 104 of FIG. 1. An anterior posterior (AP) fluoroscopic exam can be performed to identify the optimal target location. As an illustrative example, the selected target location is a T11/T12 interlaminar space or a T12/L1 interlaminar space. In some examples, the selected target location is higher than the T11/T12 interlaminar space. In some examples, the selected target location is lower than the T12/L1 interlaminar space. In certain examples, the selected target location is a T7 interlaminar space. In some further examples, the selected target location is a T9/T10 interlaminar space.

In some examples, before step 802 is performed, the method 800 can include some initial steps of placing the patient P face down on the table 102 with their back exposed, as shown in FIG. 1. An IV of fluid and light sedation can be administered to the patient P, and the patient P's vital signs can be monitored while the patient P rests on the table 102. Once these initial steps are completed, step 802 is performed to examine the patient P's spine to identify the target location by using the fluoroscopy imaging generated on the display device 108.

Next, the method 800 includes a step 804 of positioning the device 200 over the selected target location. FIG. 9 is a fluoroscopy image 900 of the patient P's spine 902 generated on the display device 108. FIG. 9 shows the device 200 placed over a selected target location 904. As described above, the pin 208 is a hollow cylindrical tube made from a material that is visible in the fluoroscopy image 900. In step 804, the pin 208 is a central point of the device 200 that is positioned over the selected target location 904 such that the pin 208 can be seen in the fluoroscopy image 900 as encircling the selected target location 904.

Next, the method 800 includes a step 806 of adjusting the angle α separating the first and second arms 202, 204 of the device 200 to define the path on the patient P's back for inserting the epidural needle 110 to reach the epidural space of the selected target location 904. The first and second arms 202, 204 are opened while keeping the pin 208 stationary over the selected target location 904 so that each of the first and second arm 202, 204 has one hole 206 medial to the most proximal pedicle, which can be seen in the fluoroscopy image 900. In some examples, the first and second arms 202, 204 are not be opened symmetrically relative to the patient P's spine such as when the patient P's spine has a sideways curvature (i.e., scoliosis).

As shown in FIG. 9, the one or more holes 206 on the first and second arms 202, 204 are surrounded by a material that is visible in the fluoroscopy image 900 such that the one or more holes 206 visually depict a path or runway for inserting the epidural needle 110 to reach the epidural space of the selected target location 904. Moreover, adjusting the angle α separating the first and second arms 202, 204 causes the angle of the path or runway that is visually depicted on the fluoroscopy image 900 to be adjusted for inserting the epidural needle 110.

To reach the epidural space of the selected target location 904, the epidural needle 110 is inserted at a shallow angle toward the selected target location 904. The epidural space of the selected target location 904 can be accessed by inserting the epidural needle 110 in an upward direction (i.e., cephalad) or by inserting the epidural needle 110 in a downward direction (i.e., caudal). Typically, the skin entry point for the epidural needle 110 is two disc levels below or above the selected target location 904 and about 6 to 8 cm lateral of the midline of the patient P's spine 902. By using the device 200, the desired skin entry point can be identified by viewing the material surrounding the one or more holes 206 in the fluoroscopy image 900.

Optimally, the epidural needle 110 should enter the epidural space at an angle of 30 degrees or less with respect to the midline of the patient P's spine 902. An angle of 30 degrees or less improves the probability that the SCS leads implanted through the epidural needle 110 will remain posterior as they are advanced posteriorly into the epidural space. In cases where the epidural needle 110 enters the epidural space at an angle that is greater than 30 degrees, the SCS leads can veer off the midline of the patient P's spine 902 and travel anteriorly in the epidural space which can result in an ineffective SCS therapy.

As shown in the fluoroscopy image 900 of FIG. 9, the angle α separating the first and second arms 202, 204 can be adjusted so that the holes 206 are orientated to be about 30 degrees or less with respect to the midline of the patient P's spine 902 and with the pin 208 encircling the selected target location 904. In this way, the device 200 is used to visually depict the path for inserting the epidural needle 110 into the epidural space of the selected target location 904.

Next, the method 800 includes a step 808 of inserting a writing instrument into the one or more holes 206 on the first and second arms 202, 204. Also, the writing instrument 1002 can be inserted into the hole 220 of the pin 208 to mark the selected target location 904 on the patient P's back. The writing instrument is used to mark one or more paths on the exposed skin surface for inserting the epidural needle 110.

Figure 10:
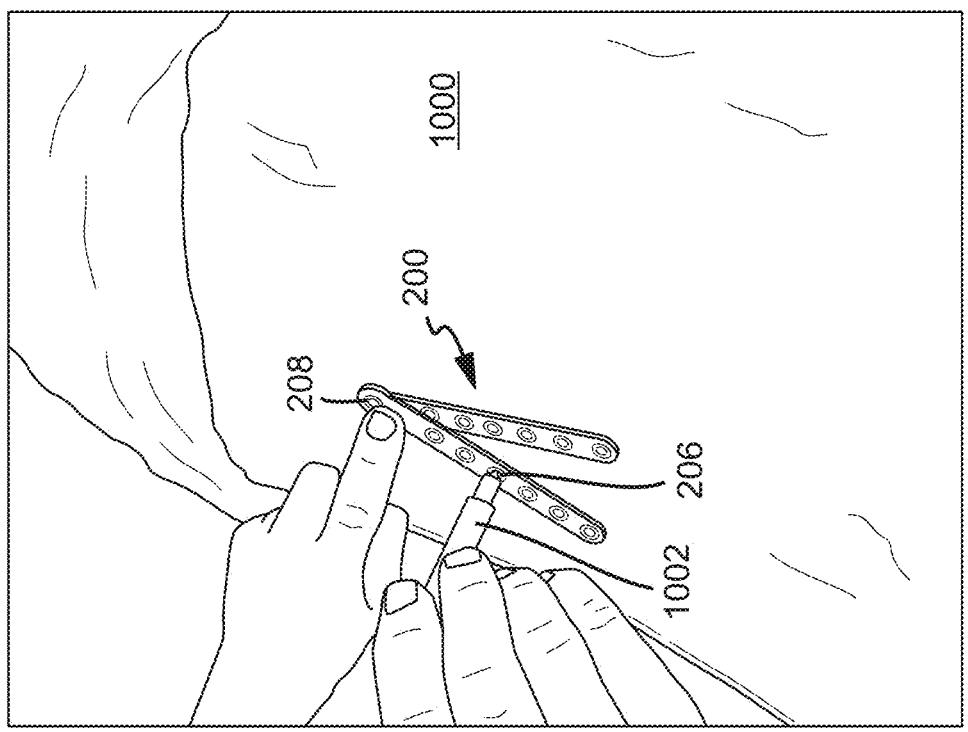
FIG. 10 shows an illustrative use of the device.

FIG. 10 shows the device 200 positioned on a skin surface 1000 of the patient P's back, and with a writing instrument 1002 being inserted into a hole 206 of the device 200 to mark a path on the skin surface 1000 for inserting the epidural needle 110.

The writing instrument 1002 applies ink to the skin surface 1000 that is visible on the skin surface 1000 after the device 200 is removed. In some examples, the writing instrument 1002 applies a metallic ink that can be seen in the fluoroscopy image generated by the display device 108 after the device 200 is removed from the skin surface 1000.

Figure 11:
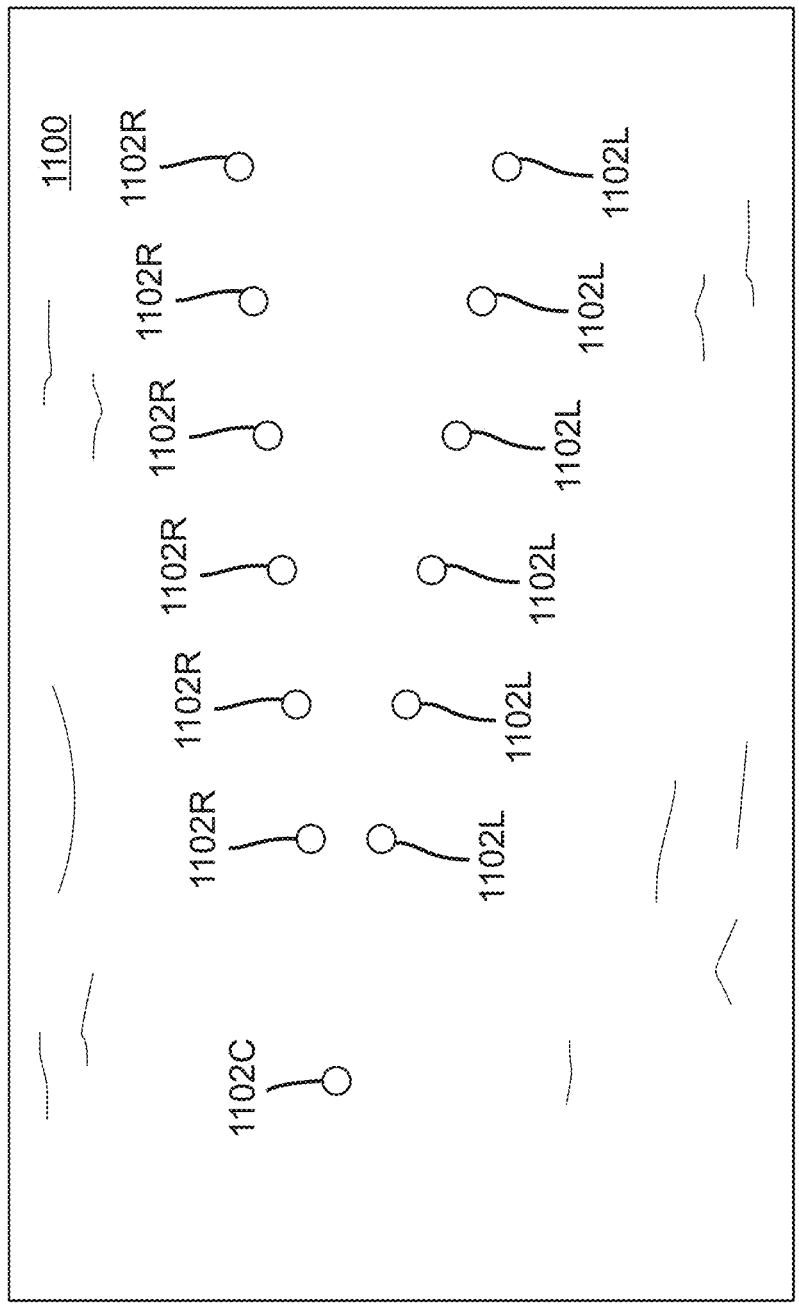
FIG. 11 is a view of a patient's back with markings made after the illustrative use of the device shown in FIG. 10.

FIG. 11 is a view of a skin surface 1100 with markings 1102 made from using the device 200 and writing instrument 1002 shown in FIG. 10. The markings 1102 provide a V shape pattern on the skin surface 1100. The V shape pattern illustrates two paths for inserting two leads into a selected target location where a central marking 1102C is drawn. The central marking 1102C can be drawn by inserting the writing instrument 1002 of FIG. 10 into the hole 220 of the pin 208. A first path for implanting a first lead is defined by the markings 1102R on the right side of the V shape pattern. A second path for implanting a second lead is defined by the markings 1102L on the left side of the V shape pattern. During the procedure of implanting the first and second leads, the epidural needle 110 can be first inserted into the selected target location by following the markings 1102R. Thereafter, the epidural needle 110 can be removed and reinserted into the selected target location by following the markings 1102L.

As shown in FIG. 11, the markings 1102C, 1102R, and 1102L each have a circular shape in view of the circular shape of the holes 206. Thus, the path that is marked on the skin surface 1100 can include a plurality of dots that are drawn by the writing instrument 1002.

In alternative examples in which the holes 206 on the first and second arms 202, 204 can have different shapes or sizes, the markings 1102C, 1102R, and 1102L will similarly have different shapes or sizes. In examples, where the first and second arms 202, 204 each include a single longitudinal slot that extends along the lengths of the first and second arms 202, 204, the markings 1102R, 1102L are linear lines that point toward the central marking 1102C defined by the shape of the hole 220 of the pin 208. Accordingly, additional shapes, sizes, and orientations are possible for the markings 1102 drawn on the skin surface 1100 using the device 200.

After the markings 1102 are made on the patient P's back from using the device 200, the physician MD can perform a procedure to implant one or more leads into the patient P's epidural space for SCS. For example, once the skin surface 1100 has been marked, a skin entry point is anesthetized using a small anesthetic needle (e.g., a 25 G to 27 G needle). As described above, the skin entry point is typically two disc levels below or above the selected target location and about 6 to 8 cm lateral of the midline of the patient P's spine. The skin entry point can be identified by the physician MD from viewing the markings 1102 on the patient P's back. For example, the distances D1-D6 shown in FIG. 4 can help identify the appropriate skin entry point.

Thereafter, a longer anesthetic needle (e.g., a 22 G needle) is inserted and advanced at an appropriate angle (e.g., 30 degrees) using the markings 1102 to advance the needle to the lamina surface next to the spinous process immediately below the selected target location (e.g., the T11/T12 or T12/L1 interlaminar space). Once the periosteum is identified, the tip of the longer anesthetic needle is used to inject local anesthesia onto the periosteum and the longer anesthetic needle is then withdrawn from the paravertebral muscles. The position of the longer anesthetic needle is viewed in anteroposterior (AP) and lateral fluoroscopy images displayed on the display device 108 before injecting local anesthesia to prevent accidentally injecting the anesthesia into the spinal canal. Once the paravertebral tract is anesthetized, an entry skin hole for the epidural needle 110 can be made using a 16 G needle of #11 surgical blade.

The physician MD can use the markings 1102 to guide the insertion of the epidural needle 110 into the patient P's epidural space before implanting the one or more leads through the epidural needle 110. For example, epidural needle 110 is passed through the skin surface and advanced at the angle (e.g., 30 degrees) relative to the patient P's spine defined by the markings 1102R on the right side of the patient P's spine or by the markings 1102L on the left side of the patient P's spine. In this manner, the markings 1102 can help guide the insertion of the epidural needle 110 such that it is advanced toward the epidural space of the selected target location (e.g., the T1/T12 or T12/L1 interlaminar space) marked by the central marking 1102C.

Advantageously, the device 200 can be used as a protractor to determine the best angle for inserting the epidural needle 110 while viewing fluoroscopy imaging. Also, the markings 1102 that can be made from using the device 200 can help guide inexperienced practitioners insert the epidural needle 110 such that it is passed through the skin and advanced at the correct angle (e.g., 30 degrees) toward the lamina next to the spinous process of the selected target location until the lamina can be felt by the practitioner from using the epidural needle 110.

In addition to using the markings 1102, the practitioner can also use the fluoroscopy imaging generated on the display device 108 (see FIG. 1) to see the advancement of the epidural needle 110. The epidural needle 110 should appear in the fluoroscopy imaging as advancing directly over the pedicle near the skin entry point and then advancing just medial to the next pedicle as it approaches the lamina next to the spinous process immediately below the selected target location. The location of the epidural needle 110 can be confirmed using the AP and lateral fluoroscopic views displayed on the display device 108. After the epidural needle is advanced to the selected target location, the one or more leads are threaded through the epidural needle 110 for implanting the distal ends of the leads into the patient P's epidural space.

Figure 12:
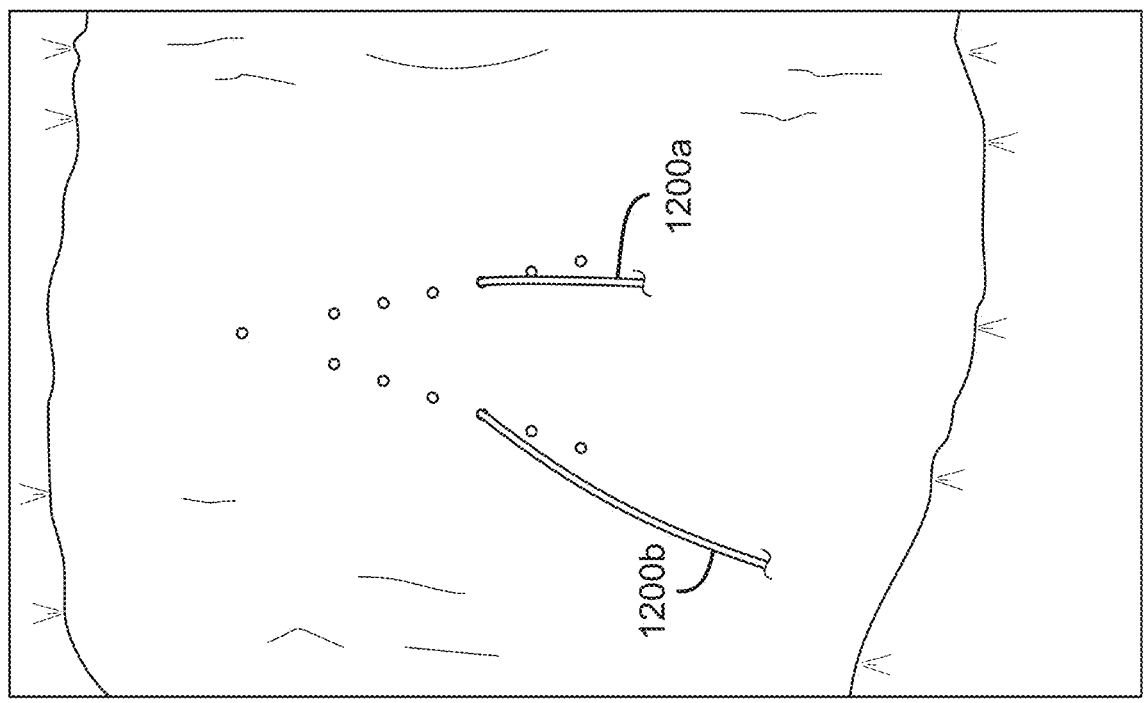
FIG. 12 is another view of the patient's back after the temporary leads for SCS have been implanted into the epidural space of the patient's spine.

FIG. 12 is another view of the patient's back after one or more leads 1200 have been implanted into the selected target location. In the example shown in FIG. 12, two leads 1200*a*, 1200*b* have been implanted into the selected target location. In this example, the leads 1200*a*, 1200*b* are insulated wire leads that are threaded through the epidural needle 110 for implanting the distal ends of the one or more leads 1200*a*, 1200*b* into the selected target location.

The proximal ends of the leads 1200*a*, 1200*b* extend from the patient P's back for connection to an external stimulator. The external stimulator generates electrical impulses that are released by contacts at the distal ends of the leads 1200*a*, 1200*b*. During SCS, the electrical impulses stimulate the nerves in the patient P's spine to block pain signals.

In certain examples, the temporary leads and external stimulator can be used for about one week to determine whether SCS is helpful in mitigating the patient P's pain. If the patient P determines that SCS helps mitigate their pain after completion of the trial, a permanent SCS system may be implanted such that the leads 1200*a*, 1200*b* are removed and replaced by permanent leads such as paddle or percutaneous leads.

The various embodiments described above are provided by way of illustration only and should not be construed to be limiting in any way. Various modifications can be made to the embodiments described above without departing from the true spirit and scope of the disclosure.

What is claimed is:

1. A device for marking a path on a skin surface for inserting an epidural needle into an epidural space, the device comprising:
    a first arm having a length extending between a proximal end and a distal end, and a first plurality of holes equally spaced apart by a fixed distance along the length of the first arm;
    a pin attached at the proximal end of the first arm, wherein the pin is a hollow cylinder made from a material that is visible in fluoroscopy imaging for providing a fixed reference point that identifies a selected target location in the epidural space; and
    a second arm having a proximal end attached to the pin allowing the first and second arms to rotate about the pin to adjust an angle separating the first and second arms, and further having a length extending from the proximal end to a distal end, and a second plurality of holes equally spaced apart by the fixed distance along the length of the second arm;
    wherein the first and second pluralities of holes on the first and second arms provide locations for marking the path on the skin surface to insert the epidural needle; and
    wherein the first and second arms include the material surrounding each hole of the first and second pluralities of holes causing the first and second pluralities of holes to visually depict a path in the fluoroscopy imaging for inserting the epidural needle to reach the selected target location identified by the pin.

2. The device of claim 1, wherein the first and second arms are rotatable about the pin between closed and opened positions, the first and second arms when in the closed position are separated by 0 degrees, the first and second arms when in the opened position are separated by 180 degrees, and the angle separating the first and second arms is adjustable between 0 and 180 degrees for marking the path on the skin surface to insert the epidural needle.

3. The device of claim 1, wherein the first and second pluralities of holes on the first and second arms are aligned when the angle separating the first and second arms is 0 degrees.

4. The device of claim 1, wherein the length of the first arm is about is about 10 cm to about 14 cm long, and the length of the second arm is about is about 10 cm to about 14 cm long.

5. The device of claim 1, wherein the lengths of the first and second arms are equal.

6. The device of claim 1, wherein the first and second arms are made from a material that is not visible in fluoroscopy imaging.

7. The device of claim 1, wherein the first and second pluralities of holes on the first and second arms provide locations for marking a V shape pattern on the skin surface.

8. The device of claim 1, wherein each hole of the first and second pluralities of holes includes a grommet.

9. A kit for marking a path on a skin surface for inserting an epidural needle into an epidural space, the kit comprising:
    a writing instrument; and
    a device comprising:
        a first arm having a length extending between a proximal end and a distal end, and a first plurality of holes equally spaced apart by a fixed distance along the length of the first arm;
        a pin attached at the proximal end of the first arm, wherein the pin is a hollow cylinder made from a material that is visible in fluoroscopy imaging for providing a fixed reference point that identifies a selected target location in the epidural space; and
        a second arm having a proximal end attached to the pin allowing the first and second arms to rotate about the pin to adjust an angle separating the first and second arms, and further having a length extending from the proximal end to a distal end, and a second plurality of holes equally spaced apart by the fixed distance along the length of the second arm;
        wherein the first and second pluralities of holes on the first and second arms provide locations for using the writing instrument to mark the path on the skin surface to insert the epidural needle; and wherein the first and second arms include the material surrounding each hole of the first and second pluralities of holes causing the first and second pluralities of holes to visually depict a path in the fluoroscopy imaging for inserting the epidural needle to reach the selected target location identified by the pin.

10. The kit of claim 9, further comprising the epidural needle.

11. The kit of claim 9, wherein the first and second pluralities of holes on the first and second arms provide locations for using the writing instrument to mark a V shape pattern on the skin surface.

12. A method of using a device to prepare a patient for implantation of a lead for spinal cord stimulation, the method comprising:
 positioning a pin hole of the device over a target location for implanting the lead, the pin hole including a material visible in fluoroscopy imaging for identifying the target location;
 adjusting an angle separating first and second arms of the device to define a path for inserting an epidural needle to reach an epidural space of the target location, proximal ends of the first and second arms being attached to the pin hole;
 inserting a writing instrument into one or more holes on the first and second arms of the device to mark the path on a skin surface of the patient; and
 inserting the epidural needle into a hole on the first arm or second arm, the hole allowing the epidural needle to advance at an angle of 30 degrees toward a spinal lamina identified by the pin hole at the target location.

13. The method of claim 12, wherein the target location is a T11/T12 interlaminar space or a T12/L1 interlaminar space.

14. The method of claim 12, further comprising marking a V shape pattern on the skin surface for inserting two leads for the spinal cord stimulation.

15. The method of claim 12, further comprising inserting the writing instrument into the pin hole of the device to mark the target location on the skin surface.

16. The method of claim 12, wherein inserting the writing instrument into the one or more holes on the first and second arms of the device includes drawing a plurality of dots for marking the path on the skin surface for inserting the epidural needle.

* * * * *